US010821425B2

(12) United States Patent
Ide et al.

(10) Patent No.: US 10,821,425 B2
(45) Date of Patent: Nov. 3, 2020

(54) TREATMENT OF AROMATIC ALKYLATION CATALYSTS

(71) Applicant: ExxonMobil Chemical Patents Inc., Baytown, TX (US)

(72) Inventors: Matthew S. Ide, Doylestown, PA (US); Brett T. Loveless, Houston, TX (US); Doron Levin, Highland Park, NJ (US); Tilman W. Beutel, Neshanic Station, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/097,666

(22) PCT Filed: Apr. 13, 2017

(86) PCT No.: PCT/US2017/027322
§ 371 (c)(1),
(2) Date: Oct. 30, 2018

(87) PCT Pub. No.: WO2017/213749
PCT Pub. Date: Dec. 14, 2017

(65) Prior Publication Data
US 2019/0314794 A1 Oct. 17, 2019

Related U.S. Application Data

(60) Provisional application No. 62/347,667, filed on Jun. 9, 2016.

(30) Foreign Application Priority Data

Jun. 26, 2016 (EP) .................................... 16181311

(51) Int. Cl.
| *B01J 29/00* | (2006.01) |
| *B01J 29/70* | (2006.01) |
| *B01J 29/08* | (2006.01) |
| *B01J 29/18* | (2006.01) |
| *B01J 35/00* | (2006.01) |
| *B01J 37/08* | (2006.01) |
| *B01J 37/14* | (2006.01) |
| *B01J 38/02* | (2006.01) |
| *B01J 38/16* | (2006.01) |
| *C07C 2/66* | (2006.01) |

(52) U.S. Cl.
CPC .......... *B01J 29/7038* (2013.01); *B01J 29/084* (2013.01); *B01J 29/088* (2013.01); *B01J 29/18* (2013.01); *B01J 29/7007* (2013.01); *B01J 35/002* (2013.01); *B01J 37/08* (2013.01); *B01J 37/14* (2013.01); *B01J 38/02* (2013.01); *B01J 38/16* (2013.01); *C07C 2/66* (2013.01); *B01J 2229/36* (2013.01); *C07C 2521/04* (2013.01); *C07C 2529/70* (2013.01)

(58) Field of Classification Search
CPC ..... C07C 2/70; C07C 15/073; C07C 2521/04; C07C 2529/70; C07C 2/66; B01J 2229/36; B01J 2229/42; B01J 29/08; B01J 29/084; B01J 29/088; B01J 29/18; B01J 29/7007; B01J 29/7038; B01J 35/002; B01J 37/08; B01J 37/082; B01J 37/14; B01J 38/02; B01J 38/12; B01J 38/16

See application file for complete search history.

(56) References Cited

U.S. PATENT DOCUMENTS

| 3,751,504 | A | 8/1973 | Keown et al. |
| 4,016,218 | A | 4/1977 | Haag et al. |
| 4,210,770 | A | 7/1980 | Marcilly |
| 4,547,605 | A | 10/1985 | Kresge et al. |
| 4,891,458 | A | 1/1990 | Innes et al. |
| 4,992,606 | A | 2/1991 | Kushnerick et al. |
| 5,258,565 | A | 11/1993 | Kresge et al. |
| 5,334,795 | A | 8/1994 | Chu et al. |
| 5,371,310 | A | 12/1994 | Bennett et al. |
| 5,453,554 | A | 9/1995 | Cheng et al. |
| 6,111,157 | A | 8/2000 | Hendriksen et al. |
| 6,878,654 | B2 * | 4/2005 | Dandekar ............... B01J 29/90 502/23 |
| 2003/0050521 | A1 | 3/2003 | Dandekar et al. |
| 2009/0030253 | A1 | 1/2009 | Xu et al. |
| 2009/0099007 | A1 | 4/2009 | Khare |
| 2013/0204060 | A1 | 8/2013 | Godsmark et al. |
| 2015/0025286 | A1 * | 1/2015 | Vincent ................. B01J 8/0496 585/449 |

FOREIGN PATENT DOCUMENTS

| JP | 61249944 A | 11/1986 |
| JP | 10052646 A | 2/1996 |
| JP | 3143920 B | 3/2001 |
| WO | 2014/182440 A | 11/2014 |

* cited by examiner

*Primary Examiner* — Sharon Pregler

(57) ABSTRACT

The present disclosure relates to a process for producing a mono-alkylated aromatic compound using a treated catalyst made by a method of this invention is disclosed. The method comprises the steps of heating an untreated catalyst in the presence of a gaseous stream having a dew point temperature less than about 5° C. to form a treated catalyst. The treatment is effective to improve the activity and selectivity of the catalyst.

15 Claims, No Drawings

TREATMENT OF AROMATIC ALKYLATION CATALYSTS

CROSS-REFERENCE TO RELATED APPLICATIONS

This application is a National Phase Application of PCT Application Serial No. PCT/US2017/027322, filed Apr. 13, 2017, which claims priorities to and the benefits of U.S. Patent Application Ser. No. 62/347,667, filed Jun. 9, 2016, and European Patent Application No. 16181311.8, filed Jun. 26, 2016, all of which are herein incorporated by reference in their entireties.

FIELD OF THE INVENTION

The present invention relates to a method of treating a catalyst, preferably an alkylation or transalkylation catalyst, and a process for production of mono-alkylated aromatic compounds using the treated catalyst.

BACKGROUND OF THE INVENTION

Mono-alkylated aromatic compounds, such as ethylbenzene and cumene, are valuable commodity chemicals which are used industrially for the production of styrene monomer and phenol respectively. Ethylbenzene may be produced by a number of different chemical processes, but one process which has achieved a significant degree of commercial success is the liquid phase processes for producing ethylbenzene from benzene and ethylene since liquid phase processes operate at a lower temperature than their vapor phase counterparts and hence tend to result in lower yields of by-products. For example, U.S. Pat. No. 4,891,458 describes the liquid phase synthesis of ethylbenzene with zeolite beta, whereas U.S. Pat. No. 5,334,795 describes the use of MCM-22 in the liquid phase synthesis of ethylbenzene. Examples of such ethylbenzene production processes are described in U.S. Pat. No. 3,751,504 (Keown), U.S. Pat. No. 4,547,605 (Kresge), and U.S. Pat. No. 4,016,218 (Haag).

Cumene has for many years been produced commercially by the liquid phase alkylation of benzene with propylene over zeolite-based catalyst systems which are more active and selective to cumene as compared to Friedel-Craft catalyst, such as phosphoric acid or aluminum chloride. For example, U.S. Pat. No. 4,992,606 describes the use of MCM-22 in the liquid phase alkylation of benzene with propylene.

Other molecular sieves known for use as liquid phase alkylation and transalkylation catalysts include MCM-36 (see U.S. Pat. No. 5,258,565), MCM-49 (see U.S. Pat. No. 5,371,310) and MCM-56 (see U.S. Pat. No. 5,453,554).

In the commercial operation of this process, the polyalkylated benzenes, including both di-ethylbenzene and di-isopropylbenzene, which are inherently co-produced with ethylbenzene and cumene in the alkylation reactor, are transalkylated with benzene to produce additional ethylbenzene or cumene either by being recycled to the alkylation reactor or by being fed to a separate transalkylation reactor. The cumene and ethylbenzene catalysts are traditionally calcined in air that contains a wide range of moisture content (as measured by relative humidity and the dew point of the air).

SUMMARY OF THE INVENTION

It has been discovered that when the moisture content of the final calcination air is high, it negatively impacts the catalytic activity and monoselectivity of the catalyst. According to the present invention, it has now been found that careful control of the dew point of the gaseous stream, such as air, for example, used in the final calcination of catalysts which have a zeolite component results in improved monoselectivity to the desired mono-alkylated aromatic compound and improved catalytic activity in aromatic alkylation processes.

In one aspect, the invention is a method of treating a catalyst, preferably an alkylation or a transalkylation catalyst, comprising a molecular sieve, the method comprising the step of heating said catalyst in the presence of a gaseous stream having a dew point temperature less than or equal to 5° C. to form a treated catalyst. Preferably, the dew point of the gaseous stream is in the range from about −40° C. up to about 5° C. Preferably, the molecular sieve is an aluminosilicate.

In another aspect, the present invention is a catalyst that is treated by any one of the methods of this invention.

In still another aspect, the present invention is a process for producing a mono-alkylated aromatic compound. The process comprises the step of contacting an alkylatable aromatic compound and an alkylating agent with a catalyst under alkylation conditions or transalkylation conditions to produce an effluent comprising said mono-alkylated aromatic compound. Such catalyst is a treated catalyst of this invention, or is a catalyst treated by any one of the methods of this invention.

In one or more embodiments, the product further comprises poly-alkylated aromatic compounds which may be transalkylated with additional alkylatable aromatic compound to produce additional mono-alkylated aromatic compound.

In one or more embodiments, the process further comprises the step of contacting said alkylatable aromatic compound or said alkylating agent with a treatment material to remove at least a portion of any impurities from said alkylatable aromatic compound and/or said alkylating agent.

DETAILED DESCRIPTION OF THE INVENTION

The present invention relates to a method of treating a catalyst used in a process for producing a mono-alkylated aromatic compound, particularly ethylbenzene or cumene, by the at least partial liquid phase alkylation of an alkylatable aromatic compound with an alkylating agent in the presence of the treated catalyst (e.g., alkylation or transalkylation catalyst) comprising a molecular sieve, such as for example, an aluminosilicate. More particularly, the method of treating the catalyst comprises the step of heating said catalyst in the presence of a gaseous stream having a dew point temperature of less than or equal to about 5° C. to form a treated catalyst. The treatment method of the present disclosure is found to be effective in improving the catalyst selectivity to the desired mono-alkylated aromatic compound, while increasing the activity of the catalyst activity.

Definitions

The term "alkylatable aromatic compound" as used herein means an aromatic compound that may receive an alkyl group. One non-limiting example of an alkylatable aromatic compound is benzene.

The term "alkylating agent" as used herein means a compound which may donate an alkyl group to an alkylatable aromatic compound. Non-limiting examples of an alkylating agent are ethylene, propylene, and butylene. Another non-limiting example is any poly-alkylated aromatic compound that is capable of donating an alkyl group to an alkylatable aromatic compound.

The term "aromatic" as used herein in reference to the alkylatable aromatic compounds which are useful herein is to be understood in accordance with its art-recognized scope which includes substituted and unsubstituted mono- and polynuclear compounds. Compounds of an aromatic character which possess a heteroatom (e.g., N or S) are also useful provided they do not act as catalyst poisons, as defined below, under the reaction conditions selected.

The term "at least partial liquid phase" as used herein, means a mixture having at least 1 wt. % liquid phase, optionally at least 5 wt. % liquid phase, at a given temperature, pressure, and composition.

The term "framework type" as used herein has the meaning described in the "Atlas of Zeolite Framework Types," by Ch. Baerlocher, W. M. Meier and D. H. Olson (Elsevier, 5th Ed., 2001).

The term "MCM-22 family material" (or "MCM-22 family molecular sieve"), as used herein, can include:

(i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001);

(ii) molecular sieves made from a common second degree building block, a 2-dimensional tiling of such MWW framework type unit cells, forming a "monolayer of one unit cell thickness," preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

Members of the MCM-22 family include, but are not limited to, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and UZM-8HS (described in U.S. Pat. No. 7,713,513); and an EMM-10 family molecular sieve (described or characterized in U.S. Pat. Nos. 7,959,899 and 8,110,176; and U.S. Patent Application Publication No. 2008/0045768), such as EMM-10, EMM-10-P, EMM-12 and EMM-13.

The term "mono-alkylated aromatic compound" means an aromatic compound that has only one alkyl substituent. Non-limiting examples of mono-alkylated aromatic compounds are ethylbenzene, iso-propylbenzene (cumene) and sec-butylbenzene.

The term "poly-alkylated aromatic compound" as used herein means an aromatic compound that has more than one alkyl substituent. A non-limiting example of a poly-alkylated aromatic compound is poly-alkylated benzene, e.g., di-ethylbenzene, tri-ethylbenzene, di-isopropylbenzene, and tri-isopropylbenzene.

The term "regenerated" when used in connection with the alkylation catalyst or the transalkylation catalyst herein means an at least partially deactivated catalyst that has been treated under controlled conditions of oxygen content and temperature to remove at least a portion of the coke deposited or to remove at least a portion of adsorbed catalyst poisons and thereby increase the catalytic activity of such material or catalyst.

The term "fresh" when used in connection with the molecular sieve, the guard bed material, the alkylation catalyst, or the transalkylation catalyst herein means the molecular sieve or such catalyst has not been used in a catalytic reaction after being manufactured.

The term "impurities" as used herein includes, but is not limited to, compounds having at least one of the following elements: nitrogen, halogens, oxygen, sulfur, arsenic, selenium, tellurium, phosphorus, and Group 1 through Group 12 metals.

Method of Treating the Catalyst

When the moisture content of the air used during final calcination is not being closely controlled, the high temperature combined with the high relative humidity and dew point of the calcination air cause the problem of a partial steaming of the zeolite component and results in the dealumination of the zeolitic component. This dealumination of the zeolitic component results in a catalyst having a lower catalytic activity and a lower selectivity to the desired mono-alkylated aromatic compound (monoselectivity) in aromatic alkylation processes. The method of treating a catalyst of this invention solves this problem.

It was unexpectedly found that during final calcination of the catalyst, as the moisture content of the gaseous stream, such as for example air, decreases (as measured by decreasing dew point temperature) the catalyst exhibits a reduction in the formation of the undesirable poly-alkylated aromatic compounds, such as for example di-isopropyl benzene (DIPB) and tri-isopropylbenzene (TIPB) with an increase in catalytic activity in a process for producing a mono-alkylated aromatic compounds.

Not to be bound by any theory, it is believed that the reduction in the formation of the undesirable poly-alkylated aromatic compounds in a process for producing a mono-alkylated aromatic compounds is due to the creation of external acid sites, either from dealumination of the molecular sieve or aluminosilicate (for example, by a loss of Bronsted acid sites inside the micropores of the molecular sieve or aluminosilicate) or a reaction of the binder (such as an alumina binder) with the zeolitic component that creates external Bronsted acid sites.

In one aspect, the invention is a method of treating a catalyst comprising a molecular sieve, preferably an alkylation or a transalkylation catalyst. The method comprising the step of heating said catalyst in the presence of a gaseous stream having a dew point temperature less than or equal to 5° C. to form a treated catalyst. The dew point of the gaseous stream is in the range from about −40° C. up to about 5° C., or in the range from about −30° C. up to about 0° C., or in the range from about −20° C. up to about 0° C. Preferably, the molecular sieve is an aluminosilicate.

The gaseous stream may comprise air in any embodiment of this invention. The gaseous stream may also comprise oxygen in a range from about 1 vol./vol. % to about 21 vol./vol. % in on or more embodiments.

The gaseous stream may further comprise at least one diluent. The diluent may be selected from the group consisting of nitrogen, helium and mixtures thereof.

The flowrate of the gaseous stream is at least 1 vol./vol. catalyst/min. in one or more embodiments.

The catalyst is heated to a temperature of greater than 300° C. or more, preferably 325° C. or more, up to a temperature of about 600° C. or more and held at that temperature for a period of time. The catalyst should not be heated to a temperature that exceeds 800° C. In one or more embodiments, the catalyst is heated for a time of at least 1 hour up to about 48 hours or more.

Moisture may be removed from air in a number of ways. One of which is the adsorption of water on a desiccant bed which contains, for example, a molecular sieve. Another way is to compress the gaseous stream such as for example air, before adsorption onto the desiccant. Thereafter, the dessicant may be regenerated by changing the pressure or temperature. Still another method is to use refrigeration to knock out the moisture from the incoming gaseous stream, such as for example air, and use it for final calcination of the catalyst.

Alkylation Catalyst and/or Transalkylation Catalyst

In another aspect, the present invention is a catalyst that is treated by any one of the methods of this invention. Preferably, the catalyst is an alkylation or a transalkylation catalyst and comprises an aluminosilicate. Such aluminosilicate may be selected from a MCM-22 family molecular sieve, faujasite, mordenite, zeolite beta, or combinations thereof.

In other embodiments, the alkylation catalyst and/or the transalkylation catalyst comprises a molecular sieve having a framework type selected from the group consisting of FAU (e.g., faujasite), MOR (e.g., mordenite), *BEA (e.g., zeolite beta) and mixtures thereof.

The faujasite molecular sieve may be selected from the group consisting of 13X, Ultrastable Y (USY) and its low sodium variant, dealuminized Y (Deal Y), Ultrahydrophobic Y (UHP-Y), rare earth exchanged Y (REY), rare earth exchanged USY (RE-USY) and mixtures thereof. The mordenite molecular sieve may be selected from the group consisting of mordenite, TEA-mordenite and mixtures thereof. The MCM-22 family molecular sieve may be selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30 and mixtures thereof.

In one or more embodiments, the catalyst is an acidic catalyst in active form and has protons. The molecular sieve can be combined in a conventional manner with an oxide binder, such as alumina or silica, such that the final alkylation catalyst and/or transalkylation contains between 1 and 100 wt. % of the molecular sieve, based on the weight of said catalyst. Alternatively, the acidic catalyst comprises greater than 0 wt. % to 99 wt. % of a binder, based on the weight of said catalyst. The binder may be a metal or a mixed metal oxide. The binder may be selected from the group consisting of alumina, silica, titania, zirconia, tungsten oxide, ceria, niobia and combinations thereof.

The effect on the catalyst of the dew point of the final calcination gaseous stream is independent of the geometry of the catalyst. Any shape, such as cylindrical or quadrulobe shape, is expected to exhibit the unexpected finding of increased monoselectivity and increased activity of the treated catalyst.

In one or more embodiments, said alkylation or transalkylation catalyst can be a fresh alkylation or transalkylation catalyst, an at least partially deactivated alkylation or transalkylation catalyst, or combinations thereof. In one or more embodiments, said at least partially deactivated alkylation or transalkylation catalyst was deactivated by coke deposition during its prior use in an alkylation or transalkylation process.

Catalyst Regeneration

As the alkylation and/or transalkylation process of the invention proceeds, the alkylation and/or transalkylation catalyst will gradually lose its alkylation activity, such that the reaction temperature required to achieve a given performance parameter, such as, for example, conversion of the alkylating agent, will increase. When the alkylation and/or transalkylation catalyst activity has decreased by some predetermined amount, typically 5% to 90% and, more preferably 10% to 50%, compared to the initial alkylation and/or transalkylation catalyst activity, the deactivated catalyst can be subjected to a regeneration procedure using any known method, such as the method disclosed in U.S. Pat. No. 6,380,119 to BASF, incorporated herein by reference.

In some embodiments, the catalyst that can be treated by the method of the present invention can be a fresh catalyst, or an at least partially deactivated catalyst, for example, a catalyst that was deactivated in a previous alkylation and/or transalkylation reaction, or can be a regenerated catalyst.

Process

In another aspect, the present invention is a process for producing a mono-alkylated aromatic compound. The process comprises the step of contacting an alkylatable aromatic compound and an alkylating agent with a catalyst under at least partial liquid phase alkylation conditions or at least partial liquid phase transalkylation conditions to produce an effluent comprising said mono-alkylated aromatic compound. Such catalyst is a treated catalyst of this invention, or is a catalyst treated by any one of the methods of this invention.

The products of the reaction which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

The alkylation process of the invention is particularly intended to produce mono-alkylated aromatic compounds, such as ethylbenzene and cumene in an alkylation step; however, the alkylation step will normally produce some poly-alkylated aromatic compounds. In one or more embodiments, the product further comprises poly-alkylated aromatic compound(s). Thus, the process preferably includes the further steps of separating the poly-alkylated aromatic compounds from the effluent, and then contacting them with additional alkylatable aromatic compound in the presence of a suitable transalkylation catalyst under at least partial transalkylation conditions in a transalkylation step. The transalkylation catalyst is preferably a molecular sieve which is selective to the production of the desired mono-alkylated aromatic compound and can, for example, employ the same or different molecular sieve as the alkylation catalyst, preferably the MCM-22 family molecular sieves (as defined herein), as well as faujasite, mordenite, or zeolite-beta, and combinations thereof.

Alkylatable Aromatic Compounds

Substituted alkylatable aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable alkylatable aromatic hydrocarbons for any one of the embodiments of this invention include benzene, naphthalene, anthracene, naphthacene, perylene, coronene, and phenanthrene, with benzene being preferred.

Generally the alkyl groups, which can be present as substituents on the aromatic compound, contain from 1 to about 22 carbon atoms and usually from about 1 to 8 carbon atoms, and most usually from about 1 to 4 carbon atoms.

Suitable alkyl substituted aromatic compounds for any one of the embodiments of this invention include toluene (also preferred), xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylated hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often, alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing substantial quantities of benzene, toluene and/or xylene constitutes a useful feed for the process of this invention.

Alkylating Agents

The alkylating agents, which are useful in one or more embodiments of this invention, generally include any aliphatic or aromatic organic compound having one or more available alkylating olefinic groups capable of reaction with the alkylatable aromatic compound. Preferably, the alkylating agent comprises an olefinic group having from 1 to 5 carbon atoms, or a poly-alkylated aromatics compound(s). Examples of suitable alkylating agents for any one of the embodiments of this invention are olefins, preferably, ethylene, propylene, the butenes, and the pentenes, and mixtures thereof; alcohols (inclusive of monoalcohols, dialcohols, trialcohols, etc.), such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Poly-alkylated aromatic compounds suitable for one or more embodiments of this invention include, but are not limited to, di-ethylbenzenes, tri-ethylbenzenes and polyethylbenzene(s), as well as di-isopropylbenzenes (DIPBs), tri-isopropylbenzenes (TIPBs) and polyisopropylbenzene(s) or mixtures thereof.

For example, a typical FCC light olefin stream possesses the following composition as shown in Table I:

TABLE I

|  | Wt. % | Mol. % |
| --- | --- | --- |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-butane | 3.3 | 2.6 |
| Butenes | 22.1 | 18.32 |
| Pentanes | 0.7 | 0.4 |

Alkylation and/or Transalkylation Conditions

The process for producing a mono-alkylated aromatic compound of this invention is conducted such that the organic reactants, i.e., the alkylatable aromatic compound and the alkylating agent, are brought into contact with a catalyst, preferably an alkylation catalyst and/or a transalkylation catalyst, in a suitable reaction zone such as, for example, in a flow reactor containing a fixed bed of the catalyst composition, under effective conditions. Such conditions include at least partial liquid phase alkylation conditions or at least partial liquid to phase transalkylation conditions.

The at least partial liquid phase conditions for alkylation can include at least one of the following: a temperature of from about 10° C. and about 400° C., or from about 10° C. to about 200° C., or from about 150° C. to about 300° C., a pressure up to about 25000 kPa, or up to about 20000 kPa, or from about 100 kPa to about 7000 kPa, or from about 689 kPa to about 4601 kPa, a molar ratio of alkylatable aromatic compound to alkylating agent of from about 0.1:1 to about 50:1, preferably from about 0.5:1 to 10:1, and a feed weight hourly space velocity (WHSV) of between about 0.1 and about 100 $hr^{-1}$, or from about 0.5 to 50 $hr^{-1}$, or from about 10 $hr^{-1}$ to about 100 $hr^{-1}$.

In one or more embodiments, the reactants can be neat, i.e., free from intentional admixture or dilution with other material, or they can include carrier gases or diluents such as, for example, hydrogen or nitrogen.

When benzene is alkylated with ethylene to produce ethylbenzene, the alkylation reaction may be carried out under at least partially liquid phase conditions for alkylation which include a temperature between about 150° C. and 300° C., or between about 200° C. and 260° C., a pressure up to about 20000 kPa, preferably from about 200 kPa to about 5600 kPa, a WHSV of from about 0.1 hr$^{-1}$ to about 50 hr$^{-1}$, or from about 1 hr$^{-1}$ and about 10 hr$^{-1}$ based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may be carried out under at least partially liquid phase conditions for alkylation which include a temperature of up to about 250° C., preferably from about 10° C. to about 200° C.; a pressure up to about 25000 kPa, preferably from about 100 kPa to about 3000 kPa; and a WHSV of from about 1 hr$^{-1}$ to about 250 hr$^{-1}$, preferably from 5 hr$^{-1}$ to 50 hr$^{-1}$, preferably from about 5 hr$^{-1}$ to about 10 hr$^{-1}$ based on the ethylene feed.

The at least partial liquid phase conditions for transalkylation can include at least one of the following: a temperature of about 100° C. to about 300° C., or from about 100° C. to about 275° C., a pressure of about 200 kPa to about 600 kPa, or about 200 kPa to about 500 kPa, a weight hourly space velocity (WHSV) based on the total feed of about 0.5 hr$^{-1}$ to about 100 hr$^{-1}$ on total feed, and aromatic/poly-alkylated aromatic compound weight ratio 1:1 to 6:1.

When the poly-alkylated aromatic compounds are poly-ethylbenzenes and are reacted with benzene to produce ethylbenzene, the transalkylation conditions include a temperature of from about 220° C. to about 260° C., a pressure of from about 300 kPa to about 400 kPa, weight hourly space velocity of 2 to 6 on total feed and benzene/PEB weight ratio 2:1 to 6:1.

When the poly-alkylated aromatic compounds are polyisopropylbenzenes (PIPBs) and are reacted with benzene to produce cumene, the conditions for transalkylation include a temperature of from about 100° C. to about 200° C., a pressure of from about 300 kPa to about 400 kPa, a weight hourly space velocity of 1 to 10 on total feed and benzene/PIPB weight ratio 1:1 to 6:1.

Guard Bed

Generally, the alkylatable aromatic compound and the alkylating agent supplied to the present process will contain some level of reactive impurities (as defined above), such as, for example, nitrogen compounds, which are small enough to enter the pores of the catalyst, preferably alkylation catalyst and/or transalkylation catalyst, and thereby poison the catalyst. Moreover, it is normal to supply all alkylatable aromatic compounds to the first alkylation and/or transalkylation reaction zone, but to divide and supply the alkylating agent between the alkylation and/or transalkylation catalyst beds. Thus, the catalyst in the first reaction zone is more likely to be poisoned by impurities. Thus, to reduce the frequency with which the catalyst in the first reaction zone must be removed for replacement, regeneration or reactivation, the present process preferably employs a separate guard bed in the first alkylation and/or transalkylation reaction zone. Alternatively, the guard bed may be upstream of and separate from the first reaction zone. The effluent from the guard bed is a treated feed, such as, for example, a treated alkylatable aromatic compound and/or a treated alkylating agent, which is then fed to the process of this invention.

The process of the invention, in one or more embodiments, further comprises the step of contacting said alkylatable aromatic compound and/or said alkylating agent with a treatment material to remove at least a portion of any impurities from said alkylatable aromatic compound or said alkylating agent. The treatment material may be selected from the group consisting of clay, resin, activated alumina, a molecular sieve and combinations thereof. The molecular sieve may be selected from the group consisting Linde X, Linde A, zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20 and combinations thereof.

The invention is more particularly described in the following numbered paragraphs.

Paragraph 1. A method of treating a catalyst which comprises a molecular sieve, the method comprises the step of heating said catalyst in the presence of a gaseous stream having a dew point temperature of less than or equal to 5° C. to form a treated catalyst.

Paragraph 2. The method of Paragraph 1, wherein said gaseous stream comprises air.

Paragraph 3. The method of any preceding Paragraph, wherein said gaseous stream comprises oxygen in a range from about 1 vol./vol. % to about 21 vol./vol. %.

Paragraph 4. The method of any preceding Paragraph, wherein said gaseous stream further comprises at least one diluent.

Paragraph 5. The method of Paragraph 4, wherein said diluent is any one of nitrogen, helium, or mixtures of two or more thereof.

Paragraph 6. The method of any preceding Paragraph, wherein said gaseous stream has a flowrate of at least 1 vol./vol. catalyst/min.

Paragraph 7. The method of any preceding Paragraph, wherein said catalyst is heated for a time of at least 1 hour up to about 48 hours.

Paragraph 8. The method of any preceding Paragraph, wherein said catalyst is heated to a temperature of greater than 300° C. up to about 600° C.

Paragraph 9. The method of any preceding Paragraph, wherein said catalyst is an acidic catalyst which has protons.

Paragraph 10. The method of any preceding Paragraph, wherein said catalyst further comprises greater than 0 wt. % to 99 wt. % of a binder, based on the weight of said catalyst.

Paragraph 11. The method of Paragraph 10, wherein said binder is metal or a mixed metal oxide.

Paragraph 12. The method of Paragraph 10, wherein said binder is any one of alumina, silica, titania, zirconia, tungsten oxide, ceria, niobia, or mixtures of two or more thereof.

Paragraph 13. The method of any preceding Paragraph, wherein said molecular sieve comprises an aluminosilicate.

Paragraph 14. The method of Paragraph 13, wherein said aluminosilicate is any one of a MCM-22 family molecular sieve, faujasite, mordenite, zeolite-beta, or combinations of two or more thereof.

Paragraph 15. The method of Paragraph 14, wherein the MCM-22 family molecular sieve is any one of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, or combinations of two or more thereof.

Paragraph 16. A catalyst treated by the method of any one of Paragraphs 1 to 15.

Paragraph 17. A process for producing a mono-alkylated aromatic compound comprising the step of contacting an alkylatable aromatic compound and an alkylating agent with a treated catalyst under at least partial liquid phase conditions for alkylation or transalkylation to produce an effluent comprising said mono-alkylated aromatic compound, wherein said treated catalyst is made by the method of any one of Paragraph 1 to 15 or a catalyst of Paragraph 16.

Paragraph 18. The process of Paragraph 17, further comprising the step of contacting said alkylatable aromatic compound or said alkylating agent with a treatment material to remove at least a portion of any impurities from said alkylatable aromatic compound or said alkylating agent.

Paragraph 19. The process of Paragraph 18, wherein said treatment material is any one of clay, resin, activated alumina, a molecular sieve, and combinations of two or more thereof.

Paragraph 20. The process of Paragraph 19, wherein said molecular sieve is any one of Linde X, Linde A, zeolite beta, faujasite, zeolite Y, Ultrastable Y, Dealuminized Y, Rare Earth Y, Ultrahydrophobic Y, mordenite, TEA-mordenite, ZSM-3, ZSM-4, ZSM-14, ZSM-18, ZSM-20, or combinations of two or more thereof.

Paragraph 21. The process of any one of Paragraph 17 to 20, wherein said alkylatable aromatic compound is benzene or toluene, or a mixture thereof.

Paragraph 22. The process of any one of Paragraph 17 to 21, wherein said alkylating agent comprises an olefinic group having 1 to 5 carbon atoms or a poly-alkylated aromatic compound.

Paragraph 23. The process of any one of Paragraph 17 to 21, wherein the alkylating agent is any one of ethylene, propylene, or a mixture thereof.

Paragraph 24. The process of any one of Paragraph 17 to 22, wherein said effluent further comprises poly-alkylated aromatic compounds.

Paragraph 25. The process of Paragraph 24, further comprising the step of separating said poly-alkylated aromatic compounds from said effluent.

Paragraph 26. The process of Paragraph 25, further comprising the step of contacting said poly-alkylated aromatic compounds and additional said alkylatable aromatic compound with a transalkylation catalyst under at least partial liquid phase conditions to produce said effluent comprising additional said mono-alkylated aromatic compound.

Paragraph 27. The process of Paragraph 26, wherein said transalkylation catalyst comprises an aluminosilicate, wherein said aluminosilicate is any one of a MCM-22 family molecular sieve, faujasite, mordenite, zeolite-beta, or combinations of two or more thereof.

Paragraph 28. The method of Paragraph 27, wherein the MCM-22 family molecular sieve is any one of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, or combinations of two or more thereof.

Paragraph 29. The process of any one of Paragraph 17 to 28, wherein said at least partial liquid phase conditions for alkylation include a temperature of from about 10° C. to about 400° C. and a pressure up to about 25000 kPa.

Paragraph 30. The process of any one of Paragraph 17 to 29, wherein said at least partial liquid phase conditions for transalkylation include a temperature of about 100° C. to about 300° C. and a pressure of from about 200 kPa to about 600 kPa.

Examples

The invention will now be more particularly described with reference to the following Examples.

Catalyst Preparation

The catalyst contained 80 wt. % MCM-49 and 20 wt. % alumina, or MCM-56 and 20 wt. % alumina that had previously undergone a high temperature treatment in flowing nitrogen and ion exchange with ammonium nitrate to convert them to acidic form. These catalysts were then calcined at high temperature in diluted air that contained a variable concentration of water. The calcination procedure utilized air and a diluent, such as nitrogen, to expose the material to a flow of approximately 1200 sccm with concentrations of oxygen ranging from 1% to 13%. In addition, the flow also contained moisture that resulted in a dew point ranging from −40° F. (−40° C.) to 80° F. (26.7° C.). The highest temperature achieved during the calcination procedure was typically at least 1000° F. (538° C.). The calcination procedure was identical for all materials discussed.

Catalyst Activity and Selectivity Evaluation

Following catalyst preparation, the activity and selectivity of each catalyst for aromatic alkylation was determined by testing the material for benzene alkylation with propylene. The test consisted of loading the dried catalyst into a batch reactor along with benzene. The reactor was then heated to 266° F. (130° C.) followed by the addition of propylene under an inert gas pressure of 300 psig (2068.43 kPa). Samples were removed periodically for the duration of the test and analyzed with gas chromatography to determine the activity and selectivity of benzene alkylation with propylene. The activity of the catalyst was evaluated by monitoring the conversion of benzene and propylene as a function of time and determining a rate constant, k, which is $10^3$ times the rate constant in units of cc $gmol^{-1}$ $hr^{-1}$. The di-isopropylbenzene (DIPB) and tri-isopropylbenzene (TIPB) selectivity of the catalyst were determined by calculating the ratio of DIPB to cumene production and TIPB to cumene production, respectively. Thus, a catalyst having a lower selectivity to the poly-alkylated aromatic compounds, such as DIPB and TIPB, is a more selective catalyst to the mono-alkylated aromatic compound, such as cumene.

Table II below shows the effect of the dew point temperature of the air used during the final calcination treatment of the catalyst containing MCM-49 on the DIPB and TIPB/IPB selectivities in a process to make cumene. An increase in the moisture content (e.g., higher dew points) of the air during final calcination of the catalyst significantly increases the production of di-isopropylbenzene (DIPB), the undesirable poly-alkylated aromatic compound, as compared to the production of isopropylbenzene (IPB), the desired mono-alkylated aromatic compound. The percent reduction in DIPB/IPB selectivity of the catalyst was over 37% when the dew point temperature of the final calcination air was −40° F. (−40° C.) as compared to a dew point temperature of 80° F. (26.7° C.). The same trend in the reduction in DIPB/IPB selectivity and TIPB/IPB selectivity of the catalyst was exhibited as a function of the reduced dew point temperature of the final calcination air. See the data in Table II for the percent reduction in DIPB/IPB and the percent reduction in TIPB/IPB as a function of the final calcination air dew points at −20° F. (−28.9° C.), 0° F. (−17.8° C.), 20° F. (−6.7° C.), 40° F. (4.4° C.), and 60° F. (15.6° C.). Thus, a significantly more monoselective MCM-49-based catalyst can be produced by treating the catalyst with air that has a lower dew point, preferably below −20° F. (−28.9° C.).

Also shown in Table II below is the effect on the relative activities of the catalyst containing MCM-49 used in a process to make cumene as a function of the moisture content (e.g., the dew point) of the final calcination air. As can be seen, the relative activities of the catalyst increased with decreasing moisture. In fact, the percent increase of the relative activity for the catalyst having a final calcination air at −40° F. (−40° C.) was 52% as compared to a final calcination air at 80° F. (26.7° C.). The same trend in the increase of the relative activity was exhibited as a function of the reduced dew point temperature of the final calcination air. See the data in Table II for the percent increase in relative activity as a function of the final calcination air dew points at −20° F. (−28.9° C.), 0° F. (−17.8° C.), 20° F. (−6.7° C.), 40° F. (4.4° C.), and 60° F. (15.6° C.). As can be seen, the higher moisture content of the air (e.g., at 80° F. (26.7° C.)) during the high temperature calcination treatment not only decreased the monoselectivity of the catalyst, but also decreased the activity of the catalyst for aromatic alkylation. Therefore, a higher activity material can be produced by decreasing the moisture content of the final air treatment, preferably below 40° F. (4.4° C.).

TABLE II

MCM-49

| Dew Point Temperature of Final Calcination Air in ° F. (° C.) | Percent Increase in Relative Activity, k | Percent Reduction in DIPB/IPB (By Weight) | Percent Reduction in TIPB/IPB (By Weight) |
|---|---|---|---|
| −40° F. (−40° C.) | 52% | 37.7% | 72.1% |
| −20° F. (−28.9° C.) | 47% | 36.6% | 70.2% |
| 0° F. (−17.8° C.) | 43% | 32.4% | 64.0% |
| 20° F. (−6.7° C.) | 44% | 27.5% | 55.4% |
| 40° F. (4.4° C.) | 42% | 20.4% | 45.0% |
| 60° F. (15.6° C.) | 19% | 12.7% | 29.7% |
| 80° F. (26.7° C.) | 0 | 0.0% | 0.0% |

Similarly, Table III below shows the reduction in DIPB/IPB and TIPB/IPB selectivities (which indicates an increase in monoselectivity to the desirable cumene product) and the increase in the relative activity with decreasing moisture content of the final calcination air for catalysts which contain MCM-56. The percent reduction in DIPB/IPB and TIPB/IPB selectivities was 31% and 58.1%, respectively, when the dew point temperature of the final calcination air was −40° F. (−40° C.) as compared to a dew point temperature of 80° F. (26.7° C.). The same trend in the reduction in DIPB/IPB selectivity and TIPB/IPB selectivity of the MCM-56-based catalyst was exhibited as a function of the reduced dew point temperature of the final calcination air. See the data in Table III below for the percent reduction in DIPB/IPB and the percent reduction in TIPB/IPB as a function of the final calcination air dew points at −20° F. (−28.9° C.), 0° F. (−17.8° C.), 20° F. (−6.7° C.), 40° F. (4.4° C.), and 60° F. (15.6° C.). Consistent with the earlier findings, a significantly more monoselective MCM-56-based catalyst can be produced by treating the catalyst with air that has a lower dew point, preferably below −20° F. (−28.9° C.).

As in the MCM-49-based catalyst, the catalysts which contain MCM-56 had an increase in relative activity as high as 25% at a dew point of −40° F. (−40° C.) as compared to 80° F. (26.7° C.). The MCM-56-based catalyst have the same trend in the increase of the relative activity was exhibited as a function of the reduced dew point temperature of the final calcination air. See the data in Table III below for the percent increase in relative activity as a function of the final calcination air dew points at −20° F. (−28.9° C.), 0° F. (−17.8° C.), 20° F. (−6.7° C.), 40° F. (4.4° C.), and 60° F. (15.6° C.).

TABLE III

MCM-56

| Dew Point Temperature in ° F. (° C.) | Percent Increase in Relative Activity, k | Percent Reduction in DIPB/IPB (By Weight) | Percent Reduction in TIPB/IPB (By Weight) |
|---|---|---|---|
| −40° F. (−40° C.) | 25% | 31.0% | 58.1% |
| 0° F. (−17.8° C.) | 19% | 21.5% | 45.2% |
| 40° F. (4.4° C.) | 18% | 13.6% | 31.0% |
| 80° F. (26.7° C.) | 0% | 0.0% | 0.0% |

Advanced characterization of the MCM-49-containing catalyst treated at −40° F. (−40° C.), 0° F. (−17.8° C.) and 80° F. (26.7° C.) dew point temperatures of the final calcination air was performed by probing the acid sites of the catalysts first with pyridine and then collidine followed by measuring the adsorption of the molecules on the Bronsted acid sites with infrared spectroscopy (IR). The catalyst was treated with pyridine to give the total amount of Bronsted acid sites, $B_{Tot}$. The pyridine was displaced by collidine to give the amount of the external Bronsted acid sites, $B_{Ext}$. The IR results in Table IV below show that as the moisture content of the air during final calcination is increased from −40° F. (−40° C.) to 80° F. (26.7° C.), the ratio between the external Bronsted acid sites and the total amount of Bronsted acid sites increased significantly. Also, as the moisture content of the air during final calcination is increased from −40° F. (−40° C.) to 80° F. (26.7° C.), the relative total Bronsted acid sites decreased by 50%, as also shown in Table IV. The MCM-49-based catalyst that were treated at 40° F. (4.40° C.) and 80° F. (26.7° C.) final calcination dew point temperature air exhibited a higher ratio of external Bronsted acid sites to total Bronsted acid sites than those treated with a moisture content of 0° F. (−17.8° C.) dew point temperature air or lower temperature. The increase in the $B_{Ext}/B_{Tot}$ likely indicates a preferential loss of Bronsted acid sites inside the micropores from dealumination of the zeolite, as observed in the 80° F. (26.7° C.) calcined sample, or potentially a reaction of the alumina binder with the zeolitic component that creates external Bronsted acid sites, as observed in the 40° F. (4.4° C.) calcined sample.

TABLE IV

Dew Point Temperature and External Bronsted Acid Site/Total Bronsted Acid Sites Ratio

| Dew Point Temperature in ° F. (° C.) | Relative Total Bronsted Acid Sites (mmol g$^{-1}$/mmol g$^{-1}$) | External Bronsted Acid Sites/Total Bronsted Acid Sites $B_{Ext}/B_{Tot}$ (mmol g$^{-1}$/mmol g$^{-1}$) |
|---|---|---|
| −40° F. (−40° C.) | 1.0 | 0.14 |
| 0° F. (−17.8° C.) | 0.98 | 0.14 |
| 40° F. (4.4° C.) | 0.85 | 0.19 |
| 80° F. (26.7° C.) | 0.50 | 0.21 |

Therefore, it was found that a more monoselective and higher alkylation activity catalyst can be produced that has a $B_{Ext}/B_{Tot}$ of below 0.19, and preferably below 0.15, by controlling the moisture content of the air during the final high temperature calcination to a dew point temperature of 0° F. (−17.8° C.) or lower temperature.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

What is claimed is:

1. A method of treating a catalyst comprising the step of heating an untreated catalyst in the presence of a gaseous stream having a dew point temperature of less than or equal to 5° C. to form a treated catalyst having a ratio of the external amount of Bronsted acid sites ($B_{Ext}$) to the total amount of Bronstead acid sites ($B_{Tot}$) of below 0.19,
    wherein said untreated catalyst comprises a fresh molecular sieve and greater than 0 wt. % to 99 wt. % of a binder, based on the weight of said catalyst, and
    wherein said fresh molecular sieve has not been used in a catalytic reaction after being manufactured and is any one of a MCM-22 family molecular sieve, faujasite, mordenite, zeolite-beta, or combinations of two or more thereof,
    wherein said gaseous stream comprises air and has an oxygen concentration in a range from 1 vol./vol. % to 21 vol./vol. %.

2. The method of claim 1, wherein said catalyst is heated to a temperature of greater than 300° C. up to about 600° C. for a time of at least 1 hour up to about 48 hours.

3. The method of claim 1, wherein said binder is any one of alumina, silica, titania, zirconia, tungsten oxide, ceria, niobia, or mixtures of two or more thereof.

4. The method of claim 1, wherein the MCM-22 family molecular sieve is any one of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, or combinations of two or more thereof.

5. The method of claim 1, wherein said catalyst is an acidic catalyst which has protons.

6. A catalyst treated by the method of claim 1 and having a ratio of the external amount of Bronsted acid sites ($B_{Ext}$) to the total amount of Bronsted acid sites ($B_{Tot}$) of below 0.19.

7. A process for producing a mono-alkylated aromatic compound comprising the step of contacting an alkylatable aromatic compound which comprises benzene and an alkylating agent with a treated catalyst having a ratio of the external amount of Bronsted acid sites ($B_{Ext}$) to the total amount of Bronstead acid sites ($B_{Tot}$) of below 0.19 under at least partial liquid phase conditions for alkylation or transalkylation to produce an effluent comprising said mono-alkylated aromatic compound,
    wherein said treated catalyst is made by the method which comprises the step of heating an untreated catalyst in the presence of a gaseous stream having a dew point temperature of less than or equal to about 5° C. to form said treated catalyst,
    wherein said untreated catalyst comprises a fresh molecular sieve and greater than 0 wt. % to 99 wt. % of a binder, based on the weight of said catalyst, and
    wherein said fresh molecular sieve has not been used in a catalytic reaction after being manufactured and is any one of a MCM-22 family molecular sieve, faujasite, mordenite, zeolite-beta, or combinations of two or more thereof, wherein said gaseous stream comprises air and has an oxygen concentration in a range from 1 vol./vol. % to 21 vol./vol. %.

8. The process of claim 7, wherein said gaseous stream further comprises at least one diluent, said diluent is any one of nitrogen, helium, or mixtures thereof.

9. The process of claim 7, wherein said alkylatable aromatic compound or said alkylating agent supplied to said process comprises impurities, the process further comprising the step of contacting said alkylatable aromatic compound or said alkylating agent with a treatment material to remove at least a portion of said impurities, said treatment material is any one of clay, resin, activated alumina, a molecular sieve, and combinations of two or more thereof.

10. The process of claim 7, wherein said alkylatable aromatic compound is benzene and said alkylating agent is ethylene and said mono-alkylated aromatic compound is ethylbenzene.

11. The process of claim 7, wherein said alkylatable aromatic compound is benzene and said alkylating agent is propylene and said mono-alkylated aromatic compound is cumene.

12. The process of claim 7, wherein said effluent further comprises poly-alkylated aromatic compounds, and said process further comprises the step of separating said poly-alkylated aromatic compounds from said effluent.

13. The process of claim 12, further comprising the step of contacting said poly-alkylated aromatic compounds and additional alkylatable aromatic compound which comprises benzene with a transalkylation catalyst under at least partial liquid phase conditions to produce said effluent comprising additional said mono-alkylated aromatic compound.

14. The process of claim 13, wherein said transalkylation catalyst comprises an aluminosilicate, wherein said aluminosilicate is any one of a MCM-22 family molecular sieve, faujasite, mordenite, zeolite-beta, or combinations of two or more thereof.

15. The process of claim 7, wherein said at least partial liquid phase conditions for alkylation include a temperature of from about 10° C. to about 400° C. and a pressure up to about 25000 kPa, or said at least partial liquid phase conditions for transalkylation include a temperature of about 100° C. to about 300° C. and a pressure of from about 200 kPa to about 600 kPa.

* * * * *